United States Patent
Goel (10) Patent No.: US 10,125,078 B1
(45) Date of Patent: Nov. 13, 2018

(54) NSAID DERIVATIVES OF OMEGA-3 POLYUNSATURATED ACIDS AS GAMMA SECRETASE MODULATORS

(71) Applicant: Jiva Pharma, Inc., Ann Arbor, MI (US)

(72) Inventor: Om P Goel, Ann Arbor, MI (US)

(73) Assignee: Jiva Pharma Inc., Ann Arbor, MI (US)

(*) Notice: Subject to any disclaimer, the term of this patent is extended or adjusted under 35 U.S.C. 154(b) by 0 days.

(21) Appl. No.: 15/386,007

(22) Filed: Dec. 21, 2016

Related U.S. Application Data (60) Provisional application No. 62/271,636, filed on Dec. 28, 2015.

(51) Int. Cl.
 C07C 69/587 (2006.01)
 C07C 61/35 (2006.01)
 C07C 57/03 (2006.01)

(52) U.S. Cl.
 CPC .............. *C07C 61/35* (2013.01); *C07C 57/03* (2013.01); *C07C 2101/02* (2013.01)

(58) Field of Classification Search
 CPC ..................................................... C07C 61/35
 USPC .......................................... 514/559; 554/224
 See application file for complete search history.

(56) References Cited

U.S. PATENT DOCUMENTS

| | | | |
|---|---|---|---|
| 8,399,516 B2 * | 3/2013 | Bryhn | A23D 9/00 514/560 |
| 9,364,465 B2 | 6/2016 | Goel | |
| 2015/0322032 A1 * | 11/2015 | Goel | C07D 309/30 514/460 |

OTHER PUBLICATIONS

Stephen D. Schmidt et al., "Aβ Measurement by Enzyme-Linked Immunosorbent Assay", Amyloid Proteins: Methods and Protocols, Methods in Molecular Biology, vol. 849, Chapter 34, pp. 507-527, Einar M. Sigurdsson et al. (eds.).

Todd E. Goldie et.al.,"γ-Secretase inhibitors and modulators", Biochimica et Biophysica Acta (BBA)—Biomembranes, vol. 1828; vol. 12, Dec. 2013, 2898-2907.

Zeljko M. Svedruzic, et. al., "Modulators of γ-Secretase Activity Can Facilitate the Toxic Side-Effects and Pathogenesis of Alzheimer's Disease"; Plos One, Jan. 1, 2013 | vol. 8 | Issue 1.

Catherine R. Burton et. al., "The Amyloid-β Rise and γ-Secretase Inhibitor Potency Depend on the Level of Substrate Expression"; Aug. 22, 2008 The Journal of Biological Chemistry 283, 22992-23003.

Daniel M. Skovronsky, et al., "Detection of a Novel Intraneuronal Pool of Insoluble Amyloid β Protein that Accumulates with Time in Culture", The Journal of Cell Biology, vol. 141, No. 4, May 18, 1998 1031-1039.

* cited by examiner

*Primary Examiner* — Deborah H Carr
(74) *Attorney, Agent, or Firm* — Technology Law, PLLC; Karen L. Kimble (57) ABSTRACT

The present invention relates to the NSAID derivatives of omega-3 fatty acids as gamma secretase modulators and their use in treating Alzheimer's disease, hypertriglyceridemia, and cardiovascular disease by reducing triglycerides, and for use as anti-inflammatory agents.

14 Claims, 3 Drawing Sheets
(3 of 3 Drawing Sheet(s) Filed in Color)

NSAID DERIVATIVES OF OMEGA-3 POLYUNSATURATED ACIDS AS GAMMA SECRETASE MODULATORS

FIELD OF THE INVENTION

The present invention relates to novel NSAID derivatives of omega-3 polyunsaturated acids as gamma secretase modulators to treat mild cases of Alzheimer's disease, to treat hypertriglyceridemia, to treat cardiovascular disease by reducing triglycerides and for use as anti-inflammatory agents.

BACKGROUND OF THE INVENTION

Alzheimer's Disease (AD)

The prevalence and incidence of Alzheimer's disease, and its devastating effects on the lives of patients and caregiver families are well known. The health care costs to society are onerous, and continues to grow with the aging population. Enormous strides have been made in understanding the pathology of the disease which leads to the build-up of amyloid plaques in the brain, which plaques are aggregates of amyloid beta (Aβ) peptides. Fundamental advances have been made in discovering inhibitors of the extra-cellular and intra-cellular neuronal biochemical enzymes such as β-secretase (BACE1) or γ-secretase (GS) to stop the amyloid or intraneuronal τ-tangles build-up; and even reverse these processes through treatment with specific monoclonal antibodies. However, in spite of massive scientific research and investments in reversing the cognitive decline of AD, these have yielded scant benefits. Consensus is emerging that the best approach would be to treat patients before the disease has progressed too far, and even before disease symptoms become apparent. Multi-targeted Alzheimer's drugs, for example dual BACE/acetylcholine esterase inhibition or GSM/PPARγ active agents would offer additional benefits (Harrie J. M. Gisjen, et al., "Secretase Inhibitors and Modulators as a Disease-Modifying Approach Against Alzheimer's Disease", *Annual Reports in Medicinal Chemistry*, 2012, 47, 55-69). Gamma secretase modulators (GSMs) cause a product shift from the longer amyloid forming Aβ peptide isoforms such as Aβ42 and Aβ40 to shorter more soluble Aβ39-Aβ37 isoforms which more easily clear from the brain than aggregate into plaques.

NSAIDS

Non-steroidal anti-inflammatory drugs, commonly known as NSAIDS are a class of drugs in ubiquitous clinical use as pain relievers or analgesics for over 60 years. The most used agents in this category are ibuprofen and naproxyn, and includes aspirin. These are usually characterized by an alkyl or alkoxyl substituted aromatic ring attached to an aliphatic —CH—($CH_3$)—COOH moiety. In early 2000's the NSAID compound tarenflurbil (R-isomer), was clinically tested in mild AD patients. It failed large scale clinical trials, which failure was attributed to its low potency at inhibiting formation of toxic Aβ42 peptide and its weak ability at crossing the blood brain barrier. Since then numerous other NSAID GSMs, such as CHF-5074 and JNJ-40418677 having potent Aβ42 $IC_{50}$ and greater brain penetration, have entered clinical trials to treat mild symptoms of AD (Harrie J. M. Gisjen, et al., "Secretase Inhibitors and Modulators as a Disease-Modifying Approach Against Alzheimer's Disease", *Annual Reports in Medicinal Chemistry*, 2012, 47, 55-69; Todd E. Goldie et al., "γ-Secretase inhibitors and modulators", Biochimica et Biophysica Acta (BBA)—Biomembranes, Volume 1828; Vol. 12, December 2013, 2898-2907).

The presence of omega-3 fatty acids, especially DHA in the brain is ubiquitous. Clinical studies in 4 year old children support the beneficial effects of docohexaenoic acid (DHA) on cognitive function (NCT 00351624; 2006-2008; sponsored by Martek BioSciences Corporation). It would be an interesting study to follow such treated children over decades regarding the incidence of onset of symptoms of Alzheimer's disease relative to the untreated group. In the meantime, it is worth exploring in a prospective study, if a DHA NSAID either alone, or in combination with another gamma secretase modulator (GSM) or other prescribed clinical agents, would slow down the decline of cognitive function in early stage AD patients.

PUFAs

Omega-3 oils or omega-3 fatty acids are naturally occurring, straight-chain (16-24 carbons) fatty carboxylic acids (PUFAs), essential for normal metabolism in humans and other animals. Since the omega-3 fatty acids are not synthesized by the human body, they are recommended to be taken as dietary supplements in 1-4 grams daily for cardiovascular health benefits, preventing strokes, and reducing blood pressure. (Delgado-Lista, J., et al., "Long Chain Omega-3 Fatty Acids and Cardiovascular Disease: A Systematic Review." *The British Journal of Nutrition*, June 2012, 107 Suppl 2, S201-13).

Omega-3 fatty acids have 3-6 conjugated carbon-carbon double bonds and are so named as the first carbon with unsaturation is 3rd carbon from the distal carboxylic acid carbon. All double bonds are in the cis configuration. Among the omega-3 fatty acids are eicosapentanenoic acid (EPA, 20 carbons, 5 conjugated double bonds), docohexaenoic acid (DHA, 22 carbons, 6 conjugated double bonds) and α-linolenic acid (ALA, 18 carbons, 3 conjugated double bonds), these are the most studied PUFAs pharmacologically.

Clearly, improvement in the treatment of AD is still sought.

BRIEF SUMMARY OF THE INVENTION

Omega-3 acids offer an unexplored and unusual structural motif of long aliphatic carbon straight-chains rich with 4-6 conjugated, all cis double bonds of 8-12 π electrons, which is in contrast to an alkyl or alkoxyl substituted benzene or naphthyl ring (6-10 π electrons) as found in the clinically used NSAIDs. Novel cyclic aliphatic NSAIDs with potent Aβ42 inhibition and excellent brain penetration are currently in clinical testing as GSMs to treat mild cases of AD. The present invention seeks to study acyclic NSAIDS derived from omega-3 acids for the same purpose. This invention uses NSAID derivatives of these omega-3 fatty acids for clinical benefits in mild cases of AD, as anti-inflammatory analgesics, and for reducing triglycerides to ameliorate cardiovascular disease.

These modified PUFA derivatives of the present invention are formed by reduction of the carboxylic acid of the omega-3s to an end methylene moiety with a leaving group X, such as a halide, mesylate or tosylate, which is displaced by an alkyl substituted acetic acid anion. The following structure depicts these present compounds in Formula (I):

Formula (I)

wherein: $R_1$ is H; and $R_2$ is $C_1$-$C_6$ straight chain or branched alkyls; $C_3$-$C_6$ cycloalkyl; $C_3$-$C_6$ fluorocycloalkyl; $C_2$-$C_6$ alkenyl; $C_2$-$C_6$-alkynyl; $C_6$-$C_{10}$ aryl unsubstituted or substituted with $C_1$-$C_6$ straight chain or branched alkyls; $C_1$-$C_6$ alkoxyl; 1,3-dioxolanyl; cyano, halo, nitro, trihaloalkyl, acyl, or acylamino; alkylaryl such as a benzyl group unsubstituted or substituted with straight chain or branched alkyl; $C_1$-$C_6$ alkoxyl; 1,3-dioxolanyl; cyano, halo, trihaloalkyl, dialkylamino; or alkyldiaryls such as diphenylmethyl.

Both R- and S-stereoisomers result in this arrangement and are included. Both isomers result from the process and can be separated.

Optionally, $R_1$ and $R_2$ of Formula (I) may be tethered together to form a 3- to 7-membered alicyclic ring, as shown in Formula (II) below. Only a single isomer results in this arrangement.

Formula (II)

wherein:
n is 1-4;
R, in Formula (I), and Formula (II) is joined from the methylene moiety formed by reduction of the carboxylic acid of one of the following polyunsaturated fatty acids (PUFAs):
cis,cis,cis-7,10,13-hexadecatrienoic acid (HTA),
cis,cis,cis-9,12,15-octadecatrienoic acid (ALA),
cis,cis,cis,cis-6,9,12,15-octadecatetraenoic acid (SDA),
cis,cis,cis-11,14,17-eicosatrienoic acid (ETE),
cis,cis,cis,cis-8,11,14,17-eicosatetraenoic acid (ETA);
cis,cis,cis,cis,cis-5,8,11,14,17-eicosapentanenoic acid (EPA),
cis,cis,cis,cis,cis-6,9,12,15,18-heneicosapentaenoic acid (HPA),
cis,cis,cis,cis,cis-7,10,13,16,19-docosapentaenoic acid (DPA),
cis,cis,cis,cis,cis,cis-4,7,10,13,16,19-docosahexaenoic acid (DHA),
cis,cis,cis,cis,cis-9,12,15,18,21-tetracosapentaeonic acid (TPA) or
cis,cis,cis,cis,cis,cis-6,9,12,15,18,21-tetracosahexaeonic acid (THA).

In Vitro Biology Introduction:

The gamma-secretase modulating activity of Jiva compounds were determined in Cell Cultures of fresh human neuroblastoma SHSY-5 cells. The enzyme-linked immunosorbent assay (ELISA) is one of the most commonly used, reliable, and sensitive methods for quantitating the A β peptides. The detailed methods for the recovery of both soluble and deposited A β from brain tissue and the subsequent quantitation of the peptides by ELISA are thoroughly described in literature such as Stephen D. Schmidt, et al., "Amyloid, Enzyme-linked immunosorbent assay, ELISA, Extraction, Quantification", *Methods in Molecular Biology*, vol. 849, DOI 10.1007/978-1-61779-551-0_34, Springer Science+Business Media, LLC 2012; Zeljko M. Svedruzic, et al., "Modulators of γ-Secretase Activity Can Facilitate the Toxic Side-Effects and Pathogenesis of Alzheimer's Disease", *PLOS ONE*, 1 Jan. 2013|Volume 8|Issue 1; Catherine R. Burton et al., "The Amyloid-β Rise and γ-Secretase Inhibitor Potency Depend on the Level of Substrate Expression" Aug. 22, 2008 *The Journal of Biological Chemistry* 283, 22992-23003.

The well-studied γ-secretase inhibitor, semagacestat (WIKI) was used as a positive control in the above assays.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary

ALA means α-linolenic acid or cis,cis,cis-9,12,15-octadecatrienoic acid, having 18 carbons, 3 cis double bonds, that is modified by reduction of the carboxylic acid to a methylene moiety to be R of Formula (I),

DHA means cis,cis,cis,cis,cis,cis-4,7,10,13,16,19-docosahexaenoic acid or docosahexaenoic acid, having 22 carbons, 6 cis double bonds, that is modified by reduction of the carboxylic acid to a methylene moiety to be R of Formula (I),

DPA means cis,cis,cis,cis,cis-7,10,13,16,19-docosapentaenoic acid or docosapentaenoic acid, having 22 carbons, 5 cis double bonds, that is modified by reduction of the carboxylic acid to a methylene moiety to be R of Formula (I),

EPA means cis,cis,cis,cis,cis-5,8,11,14,17-eicosapentanenoic acid or eicosapentanenoic acid, having 20 carbons, 5 cis double bonds, that is modified by reduction of the carboxylic acid to a methylene moiety to be R of Formula (I),

ETA means cis,cis,cis,cis-8,11,14,17-eicosatetranoic acid or eicosatetraenoic acid, having 20 carbons, 4 cis double bonds, that is modified by reduction of the carboxylic acid to a methylene moiety to be R of Formula (I),

ETE means cis,cis,cis-11,14,17-eicosatrienoic acid or eicosatrienoic acid, having 20 carbons, 3 cis double bonds, that is modified by reduction of the carboxylic acid to a methylene moiety to be R of Formula (I),

HPA means cis,cis,cis,cis,cis-6,9,12,15,18-heneicosapentaenoic acid or heneicosapentaenoic acid, having 21 carbons, 5 cis double bonds, that is modified by reduction of the carboxylic acid to a methylene moiety to be R of Formula (I):

HTA means cis,cis,cis-7,10,13-hexadecatrienoic acid, having 16 carbons, 3 cis double bonds, that is modified by reduction of the carboxylic acid to a methylene moiety to be R of Formula (I),

SDA means cis,cis,cis,cis-6,9,12,15-octadecatetraenoic acid or stearidonic acid, having 18 carbons, 4 cis double bonds, that is modified by reduction of the carboxylic acid to a methylene moiety to be R of Formula (I), THA means cis,cis,cis,cis,cis,cis-6,9,12,15,18,21-tetracosahexaeonic acid, having 24 carbons, 6 cis double bonds, that is modified by reduction of the carboxylic acid to a methylene moiety to be R of Formula (I), TPA means cis,cis,cis,cis,cis-9,12,15,18,21-tetracosapentaeonic acid, having 24 carbons, 5 cis double bonds, that is modified by reduction of the carboxylic acid to a methylene moiety to be R of Formula (I Et means ethyl
GSM means gamma secretase modulators
NSAIDS mean nonsteroidal anti-inflammatory drugs
Omega-3 fatty acids means naturally occurring, straight-chain $C_{16}$-$C_{24}$ fatty carboxylic acids
PUFA means polyunsaturated fatty acids that are either naturally occurring omega-3 fatty acids or derivatives thereof.
DIBALH means diisobutylaluminumhydride
EtOAc means ethyl acetate
GSM means gamma secretase modulators
h means hours
min means minutes
halo means Cl, Br or F
HMPA means hexamethylphosphoramide
LDA means lithium diisopropylamide
Ph means phenyl
rt means retention time
RT means room temperature or ambient temperature from about or about 22 to about 25° C.
TFA means trifluoroacetic acid
THF means tetrahydrofuran
TLC means thin layer chromatography
HRMS means high resolution mass spectroscopy
w/w means weight by weight.
w/v means weight per volume
% means by weight unless specified otherwise The present invention provides NSAID compounds of Formula (I) that are derived from the above named polyunsaturated omega-3 fatty acids (PUFAs) as gamma secretase modulators (GSM) to treat or slow down the progression of early stages of Alzheimer's disease, to treat hypertriglyceridemia, to treat cardiovascular disease by reducing triglycerides, and for use as anti-inflammatory agents.

Formula (I)

wherein: $R_1$ is H; and $R_2$ is $C_1$-$C_6$ straight chain or branched alkyls; $C_3$-$C_6$ cycloalkyl; fluoro $C_3$-$C_6$ cycloalkyl; $C_2$-$C_6$ alkenyl; $C_2$-$C_6$-alkynyl; $C_6$-$C_{10}$ aryl unsubstituted or substituted with $C_1$-$C_6$ straight chain or branched alkyls; $C_1$-$C_6$ alkoxyl; 1,3-dioxolanyl; cyano, halo, nitro, trihaloalkyl, acyl, or acylamino; alkylaryl such as a benzyl group unsubstituted or substituted with straight chain or branched alkyl; $C_1$-$C_6$ alkoxyl; 1,3-dioxolanyl; cyano, halo, trihaloalkyl, or dialkylamino; or alkyldiaryls such as diphenylmethyl.

Both R- and S-stereoisomers result in this arrangement and are included.

Optionally, $R_1$ and $R_2$ may be tethered together to form 3- to 7-membered alicyclic rings to give compounds of Formula (II), wherein n=1-4. Only a single isomer results from Formula (II):

Formula (II)

R, in Formula (I) and Formula (II), is joined from the methylene moiety formed by reduction of the carboxylic acid of one of the following polyunsaturated fatty acids (PUFAs):
cis,cis,cis-7,10,13-hexadecatrienoic acid (HTA),
cis,cis,cis-9,12,15-octadecatrienoic acid (ALA),
cis,cis,cis,cis-6,9,12,15-octadecatetraenoic acid (SDA),
cis,cis,cis-11,14,17-eicosatrienoic acid (ETE),
cis,cis,cis,cis-8,11,14,17-eicosatetraenoic acid (ETA);
cis,cis,cis,cis,cis-5,8,11,14,17-eicosapentanenoic acid (EPA),
cis,cis,cis,cis,cis-6,9,12,15,18-heneicosapentaenoic acid (HPA),
cis,cis,cis,cis,cis-7,10,13,16,19-docosapentaenoic acid (DPA),
cis,cis,cis,cis,cis,cis-4,7,10,13,16,19-docosahexaenoic acid (DHA),
cis,cis,cis,cis,cis-9,12,15,18,21-tetracosapentaeonic acid (TPA) or
cis,cis,cis,cis,cis,cis-6,9,12,15,18,21-tetracosahexaeonic acid (THA).

Omega-3 acids offer an unexplored and unusual structural motif of long aliphatic carbon straight-chains rich with 4-6 conjugated, all cis double bonds of 8-12 π electrons, which is in contrast to a substituted alkyl or alkoxyl benzene or naphthyl ring (6-10 π electrons) as found in the clinically used NSAIDs. Novel cyclic aliphatic NSAIDs with potent Aβ42 inhibition and excellent brain penetration are currently in clinical testing as GSMs to treat mild cases of AD. The present invention seeks to evaluate acyclic NSAIDS derived from omega-3 acids for the same purpose.

This invention will be further clarified by a consideration of the following examples of synthesis of compounds of Formula (I) and Formula (II), which are intended to be purely exemplary of the present invention.

Synthesis Overview:

The NSAID compounds of the present invention were synthesized according to Scheme 1 and Scheme 2 below.

Formula (I)

d) KOH, EtOH, water, HCl for $R_3$=Et; TFA, $CH_2Cl_2$ for $R_3$=t-butyl

Scheme 1.

R=omega-3 ethyl esters;
a) LAH, THF, 0° C.; b) $CBr_4$, $P(Ph)_3$, $CH_2Cl_2$, 0° C.

$R_3$ is ethyl
c) LDA, THF, −78° C. to RT
$R_1$ is H;
$R_2$ is $C_1$-$C_6$ straight chain or branched alkyls; $C_3$-$C_6$ cycloalkyl; fluoro $C_3$-$C_6$ cycloalkyl; $C_2$-$C_6$ alkenyl; $C_2$-$C_6$-alkynyl; $C_6$-$C_{10}$ aryl unsubstituted or substituted with $C_1$-$C_6$ straight chain or branched alkyls; $C_1$-$C_6$ alkoxyl; 1,3-dioxolanyl; cyano, halo, nitro, trihaloalkyl, acyl, or acylamino; alkylaryl such as a benzyl group unsubstituted or substituted with straight chain or branched alkyl; $C_1$-$C_6$ alkoxyl; 1,3-dioxolanyl; cyano, halo, trihaloalkyl, or dialkylamino; or alkyldiaryls such as diphenylmethyl

Scheme 2.

Formula (II)

wherein n=1-4; R and $R_3$ are defined as before.

The eicosapentaenoic (EPA) fibrate analogs and the linolenic (ALA) fibrate analogs were prepared in 3-4 steps from EPA ester and ALA acid. The EPA ester and ALA acid were first reduced to the alcohol with lithium aluminum hydride. The alcohol was converted to the bromide with triphenylphospine and carbon tetrabromide. The bromides were then alkylated with either the dianion of cyclopropylacetic acid or the anion of tert-butyl cyclopropanecarboxylate. Attempts to use the methyl or ethyl esters failed to generate the correct product. In the case of the alkylation with tert-butyl cyclopropanecarboxylate, the t-butyl group was removed with TFA to produce the corresponding acid. The alkylation with the dianion of cyclopropylacetic acid required longer reaction times and heating to 50° C. to drive the reaction. This led to some decomposition of the product which complicated the purification.

The figure below outlines the synthesis.

Synthesis:

EPA cyclopropyl-fibrate
JIVA 0026 and

EPA cyclopropyl acetic acid-fibrate
JIVA 0028

ALA cyclopropyl-fibrate
JIVA 0027 and

ALA cyclopropyl acetic acid-fibrate
JIVA 0029

The general process schemes are provided in greater detail in the following examples. It should be noted that the syntheses of these compounds are long, and purifications tedious and time consuming.

EXPERIMENTAL SECTION

Example 1: ALA Cyclopropyl-fibrate t-Butyl Ester: JIVA0025 and ALA Cyclopropyl Fibrate: JIVA0027: Formula (II)

Part 1: Preparation of ALA Alcohol of the Formula

An oven-dried 100 mL round bottomed flask was charged with lithium aluminum hydride (2.04 g, 53.87 mmol) in anhydrous THF (20 mL). The flask was cooled to 0° C. with an ice-water bath. To this suspension was added dropwise a solution of ALA acid (5.00 g, 17.96 mmol) in THF (20 mL) via syringe under argon. When the addition was complete, the mixture was allowed to warm to RT and stirred for 4 h. The reaction was then quenched at 0° C. by slow dropwise addition of saturated aqueous solution of sodium sulfate (10 mL). The mixture was allowed to stir for 0.5 h at RT and then filtered through a Buchner funnel. The residue was rinsed with THF. The filtrate and washings were combined and concentrated under reduced pressure to obtain 4.75 g of ALA alcohol as a colorless oil (100%), and is further characterized by:

$^1$H NMR (300 MHz, CDCl$_3$/TMS): δ 5.45-5.25 (m, 6H), 3.63 (t, J=6.6 Hz, 2H), 2.81 (t, J=5.7 Hz, 4H), 2.15-2.00 (m, 4H), 1.62-1.45 (m, 3H), 1.42-1.20 (m, 10H), 0.98 (t, J=7.7 Hz, 3H).

$^{13}$C NMR (75 MHz, CDCl$_3$/TMS): δ 131.7, 130.1, 128.1, 127.5, 126.9, 62.9, 32.7, 29.6, 29.5, 29.4, 29.2, 27.2, 25.7, 25.6, 25.5, 20.5, 14.3.

Part 2: Preparation of ALA Bromide of the Formula

To a solution of ALA alcohol (4.75 g, 17.96 mmol) [as made in Example 1, Part 1] and carbon tetrabromide (6.55 g, 19.76 mmol) in anhydrous methylene chloride (30 mL) was added triphenylphosphine (5.18 g, 19.76 mmol) in 4 portions, at 0° C., with an interval of 15 min in between each portion. The resulting reaction mixture was allowed to stir at 0° C. The reaction was monitored by TLC. After 4 h the reaction mixture was concentrated under reduced pressure. Hexanes (50 mL) was added and the mixture was cooled and filtered to remove triphenylphosphine oxide. The filtrate and washings were concentrated under reduced pressure to give crude product as yellow oil, then purified by silica gel column chromatography (1% ethyl acetate/heptane) to provide ALA bromide as colorless oil (5.54 g, 94% yield), and is further characterized by:

$^1$H NMR (300 MHz, CDCl$_3$/TMS): δ 5.45-5.25 (m, 6H), 3.40 (t, J=6.9 Hz, 2H), 2.81 (t, J=5.6 Hz, 4H), 2.14-2.00 (m, 4H), 1.95-1.80 (m, 2H), 1.48-1.15 (m, 10H), 0.98 (t, J=7.7 Hz, 3H).

$^{13}$C NMR (75 MHz, CDCl$_3$/TMS): δ 131.7, 130.0, 128.1, 128.0, 127.5, 126.9, 33.9, 32.8, 29.5, 29.3, 29.1, 28.7, 28.1, 27.2, 25.6, 25.5, 20.5, 14.3.

Part 3: Preparation of ALA Iodide: 18-Iodo-octadeca-3,6,9-triene, Shown by the Formula ALA alcohol [as made in Example 1, Part 1], (3.22 g, 12.2 mmol) was added to a mixture of iodine (4.64 g, 18.3 mmol), triphenylphosphine (4.79 g, 18.3 mmol), and imidazole (1.66 g, 24.4 mmol) in 40 mL of diethyl ether and acetonitrile (3:1) at 5° C. The resulting reaction mixture was allowed to warm to RT and stirred for 1 h. The reaction mixture was diluted with ether (150 mL) and extracted with 5% sodium bicarbonate solution and water (40 mL). The ether solution was dried over sodium sulfate, filtered, and concentrated under reduced pressure to give crude product as yellow oil, then purified by silica gel column chromatography (1% ethyl acetate/heptane) provide ALA iodide) as colorless oil (4.30 g, 94% yield), and further characterized by:

$^1$H NMR (300 MHz, CDCl$_3$/TMS): δ 5.45-5.25 (m, 6H), 3.18 (t, J=6.9 Hz, 2H), 2.81 (t, J=5.6 Hz, 4H), 2.14-2.00 (m, 4H), 1.95-1.80 (m, 2H), 1.48-1.15 (m, 10H), 0.98 (t, J=7.7 Hz, 3H).

Part 4: Preparation of ALA Cyclopropyl-fibrate t-butyl Ester: JIVA0025 of the Formula To a stirred solution of t-butyl cyclopropanecarboxylate (2.84 g, 20.0 mmol), and ALA bromide (5.00 g, 15.3 mmol) [as made in Example 1, Part 2] in anhydrous THF (100 mL) cooled at −78° C., was added dropwise, 2.0M LDA (10 mL, 20.0 mmol). After addition, the reaction mixture was stirred at −78° C. for 20 mins and then stirred at RT for two days. The reaction mixture was cooled to −78° C. and more LDA (2 mL, 4.0 mL) was added. The mixture was continued to stir at RT for one more day, and then poured into ice-cold saturated ammonium chloride solution (300 mL) and extracted with methyl t-butyl ether (2×200 mL). The combined organic extracts were washed with brine (300 mL), dried over sodium sulfate, and concentrated under reduced pressure. The crude product was purified through a flash chromatography on silica-gel eluted with heptane/dichloromethane (from 50:1 to 5:1) to give the desired ester JIVA0025 (3.51 g, 59% yield) as a colorless oil, and further characterized by:

| Analysis: | |
|---|---|
| Appearance: | colorless oil |
| Chemical Formula: | C$_{26}$H$_{44}$O$_2$ |
| Molecular Weight: | 388.64 |
| Chromatographic purity (HPLC): | 98.6% (rt = 9.632 min, isocratic MeOH, Synergi Max-RP, 5 μ, 4.6 × 150 mm, 1.0 mL/min, 5 μL injection, 40° C., UV detection, 210 nm) |
| $^1$H NMR (300 MHz, CDCl$_3$/TMS): | δ 5.36 (m, 6 H), 2.81 (t, 4 H, J = 5.7 Hz), 2.07 (m, 4 H), 1.42 (s, 9 H), 1.26 (m, 14 H), 1.09 (dd, 2 H, J = 6.3, 3.9 Hz), 0.98 (t, 3 H, J = 7.5 Hz), 0.58 (dd, 2 H, J = 6.3, 3.9 Hz). |

Part 5: Preparation of ALA Cyclopropyl Fibrate: JIVA0027: Formula (II) of the Formula To a stirred solution of ALA cyclopropyl-fibrate t-butyl ester (6.60 g, 17.0 mmol) [as made in Example 1, Part 4] in anhydrous dichloromethane (150 mL), cooled in an ice bath, was added TFA (6.68 g, 58.6 mmol) dropwise, and the mixture was stirred at RT for two days. The reaction mixture was concentrated under reduced pressure and the residue was dissolved in methyl t-butyl ether (150 mL). The resulting mixture was washed with water (2×100 mL), brine (100 mL), dried over sodium sulfate and concentrated under reduced pressure. The residue was purified through a silica-gel flash chromatography eluted with heptane/ethyl acetate (from 20:1 to 10:1) to give the desired acid JIVA0027 (4.05 g, 72% yield) as a yellowish oil, and further characterized by:

| Analysis: | |
|---|---|
| Appearance: | light yellow oil |
| Chemical Formula: | C$_{22}$H$_{36}$O$_2$ |
| Molecular Weight: | 332.53 |
| Chromatographic purity (HPLC): | 99.4% (rt = 11.840 min, isocratic MeOH, Synergi Max-RP, 5 μ 4.6 × 150 mm, 1.0 mL/min, 5 μL injection, 40° C., UV detection, 210 nm) |
| HRMS (ESI): | Calculated for C$_{22}$H$_{37}$O$_2$ (M+H)$^+$: 333.2788, found 333.2792. |
| $^1$H NMR (300 MHz, CDCl$_3$/TMS): | δ 11.80 (s, br, 1 H), 5.36 (m, 6 H), 2.81 (t, 4 H, J = 5.4 Hz), 2.08 (m, 4 H), 1.48 (m, 4 H), 1.26 (m, 12 H), 0.98 (t, 3 H, J =7.5 Hz), 0.75 (dd, 2 H, J = 6.6, 3.6 Hz). |

Example 2: EPA Cyclopropyl-fibrate: JIVA0026: Formula (II); and EPA Cyclopropyl Acetic Acid Fibrate: JIVA0028; Formula (II)

Part 1: Preparation of EPA Alcohol of the Formula

An oven-dried 100 mL round bottomed flask was charged with lithium aluminum hydride (0.76 g, 20 mmol) in anhydrous THF (15 mL). The flask was then cooled to 0° C. with an ice-water bath. To this suspension was added dropwise a solution of EPA ethyl ester (3.30 g, 10 mmol) in THF (10 mL) via syringe under argon. When the addition was complete, the mixture was allowed to stir for 3 h at 0° C. The reaction was monitored by TLC. After the reaction was complete, it was quenched at 0° C. by slow dropwise addition of saturated aqueous solution of sodium sulfate (4 mL). The mixture was then allowed to stir for 0.5 h at RT, and then filtered through a Buchner funnel. The residue was rinsed with THF. The filtrate and washings were combined and concentrated under reduced pressure to obtain 2.88 g of EPA alcohol as yellow oil (100% yield), and further characterized by:

$^1$H NMR (300 MHz, CDCl$_3$/TMS): δ 5.50-5.20 (m, 10H), 3.65 (t, J=6.5 Hz, 2H), 2.92-2.75 (m, 8H), 2.18-2.02 (m, 4H), 1.64-1.54 (m, 2H), 1.64-1.38 (m, 2H), 0.98 (t, J=7.7 Hz, 3H).

$^{13}$C NMR (75 MHz, CDCl$_3$/TMS): δ 131.8, 129.7, 128.4, 128.2, 128.0, 127.93, 127.86, 127.81, 127.68, 126.8, 62.8, 32.3, 26.9, 25.7, 25.6, 25.5, 20.5, 14.3.

Part 2: Preparation of EPA Bromide of the Formula

To a solution of EPA alcohol (2.88 g, 10 mmol) [as made in Example 2, Part 1] and carbon tetrabromide (3.65 g, 11 mmol) in anhydrous methylene chloride (20 mL) was added triphenylphosphine (2.89 g, 11 mmol) in 4 portions with an interval of 15 min in between each portion at 0° C. The resulting reaction mixture was allowed to stir at 0° C. The reaction was monitored by TLC. After 4 h the reaction mixture was concentrated under reduced pressure. Hexanes (30 mL) was added and the mixture was cooled and filtered to remove triphenylphosphine oxide. The filtrate and washings were concentrated under reduced pressure to give crude product as yellow oil, then purified by silica gel column chromatography (1% ethyl acetate/heptane) to provide EPA bromide as a colorless oil (3.27 g, 93% yield), and is further characterized by:

$^1$H NMR (300 MHz, CDCl$_3$/TMS): δ 5.45-5.22 (m, 10H), 3.41 (t, J=6.8 Hz, 2H), 2.90-2.70 (m, 8H), 2.15-2.00 (m, 4H), 1.95-1.81 (m, 2H), 1.58-1.42 (m, 2H), 0.98 (t, J=7.7 Hz, 3H).

$^{13}$C NMR (75 MHz, CDCl$_3$/TMS): δ 131.8, 129.2, 128.4, 128.2, 128.0, 127.9, 127.7, 126.8, 33.6, 32.3, 28.0, 26.3, 25.6, 25.5, 20.5, 14.3.

Part 3: Preparation of EPA Cyclopropyl-fibrate t-butyl Ester: JIVA0024; of the Formula To a solution of diisopropylamine (0.96 g, 9.4 mmol) in dry THF (8 mL) was added 2.5M n-BuLi in hexanes (3.88 mL, 9.68 mmol) via a syringe, and under argon at 0° C. The mixture was stirred at 0° C. for 0.5 h, and cooled to −70° C. t-Butyl cyclopropanecarboxylate (1.22 g, 8.54 mmol) was added dropwise via a syringe. Then the cooling bath was warmed to −25° C. over 2 h. After the reaction mixture was recooled to −70° C., and EPA bromide (1.00 g, 2.84 mmol) [as made in Example 2, Part2] was added dropwise. After addition, the reaction mixture was stirred and warmed to −5° C. over 6.5 hours. Saturated Na$_2$SO$_4$ aqueous solution (2 mL) was added to quench the reaction, then diluted with EtOAc (40 mL), washed with water (20 mL), and brine (10 mL). The aqueous layer was extracted with EtOAc (20 mL). The combined organic extracts were dried over magnesium sulfate, and concentrated under reduced pressure. The crude product was purified through a flash chromatography on silica gel eluted with 1% EtOAc/heptane to give the desired ester JIVA0024 (0.53 g, 45% yield) as a colorless oil, and further characterized by:

| Analysis: | |
|---|---|
| Appearance: | colorless oil |
| Chemical Formula: | C$_{28}$H$_{44}$O$_2$ |
| Molecular Weight: | 412.65 |
| Chromatographic purity (HPLC): | 96.7% (rt = 8.149 min, Alltima C-18, 5 μ, 4.6 × 150 mm, 1.0 mL/min, 5 μL injection, 40° C., UV detection, 210 nm). |
| $^1$H NMR (300 MHz, CDCl$_3$/TMS): | δ 5.45-5.20 (m, 10 H), 2.88-2.75 (m, 8 H), 2.15-2.00 (m, 4 H), 1.42 (s, 9 H), 1.50-1.30 (m, 6 H), 1.10 (dd, 2 H, J = 6.3, 3.9 Hz), 1.00 (t, 3 H, J = 7.5 Hz), 0.59 (dd, 2 H, J = 6.3, 3.9 Hz). |

Example 3: Preparation of EPA Cyclopropyl-fibrate: JIVA0026: Formula (II) of the Formula To a stirred solution of EPA cyclopropyl fibrate t-butyl ester (2.82 g, 6.83 mmol) [as made in Example 2, Part 3] in anhydrous dichloromethane (10 mL) was added TFA (10 mL), and mixture stirred at RT for 1 h. The reaction mixture was concentrated under reduced pressure and the residue was purified through a silica gel flash chromatography eluted with heptane/ethyl acetate (from 100:1 to 20:1) to give the desired acid JIVA0026 (1.84 g, 75% yield) as a pale yellow oil, and further characterized by:

| Analysis: | |
|---|---|
| Appearance: | light yellow oil |
| Chemical Formula: | C$_{24}$H$_{36}$O$_2$ |
| Molecular Weight: | 356.54 |
| Chromatographic purity (HPLC): | 98.3% (rt = 16.917 min, gradient MeOH/DIUF water 90 to 100% over 15 min., Synergi Max-RP, 5 μ, 4.6 × 150 mm 1.0 mL/min, 5 μL injection, 40° C., UV detection, 210 nm) |
| HRMS (ESI): | Calculated for C$_{22}$H$_{37}$O$_2$ (M+H)$^+$: 357.54 found: 357.54 |
| $^1$H NMR (300 MHz, CDCl$_3$/TMS): | δ 5.50-5.10 (m, 10 H), 2.90-2.74 (m, 8 H), 2.14-2.00 (m, 4 H), 1.56-1.42 (m, 4 H), 1.40-1.22 (m, 6 H), 0.97 (t, 3 H, J = 7.5 Hz), 0.75 (dd, 2 H, J = 6.9, 3.6 Hz). |

Example 4: EPA Cyclopropyl-acetic acid-fibrate: JIVA0028: Formula (II)

To a stirred solution of cyclopropyl acetic acid (2.93 g, 29.3 mmol) in anhydrous THF (100 mL) cooled at −78° C. was added 2.0M LDA in THF (29.3 mL, 58.6 mmol). After addition, the reaction mixture was allowed to equilibrate to RT (30 mins) and then heated at 50° C. for one hour to complete formation of the dianion. The mixture was cooled again to −78° C. and EPA bromide (10.3 g, 29.3 mmol) [as made in Example 2, Part 2] was added dropwise. The reaction mixture was stirred at RT overnight and then at 50° C. for four days. The reaction mixture was cooled to RT and then poured into ice-cold 1N hydrochloric acid (300 mL), and extracted with methyl t-butyl ether (2×300 mL). The combined organic extracts were washed with brine (300 mL), dried over sodium sulfate and concentrated under reduced pressure, followed by purification through a silica gel flash chromatography eluted with heptane/ethyl acetate (from 50:1 to 10:1) to give the desired acid JIVA0028 (4.17 g 38% total yield) as a light yellow oil and further characterized by:

| Analysis: | |
|---|---|
| Appearance: | light yellow oil |
| Chemical Formula: | $C_{25}H_{38}O_2$ |
| Molecular Weight: | 370.58 |
| Chromatographic purity (HPLC): | 95.6% (rt = 13.995 min, gradient (10 mM NH$_4$OAc in MeOH)/DIUF water from 60/40 to 100% MeOH in 10 min, hold for 10 min, and back, Synergi Max-RP, 5 μ, 4.6 × 150 mm, 1.0 mL/min, 5 μL injection, 40° C., UV detection, 210 nm) |
| HRMS (ESI): | Calculated for $C_{25}H_{37}O_2$ (M−H)$^−$: 369.2799, found 369.2797. |
| $^1$H NMR (300 MHz, CDCl$_3$/TMS): | δ 11.36 (s, br, 1 H), 5.36 (m, 10 H), 2.83 (m, 8 H), 2.07 (m, 4 H), 1.60 (m, 4 H), 1.39 (m, 4 H), 0.95 (t, 3 H, J = 7.5 Hz), 0.55 (m, 2 H), 0.32 (m, 1 H), 0.16 (m, 1 H). |

Example 5: Preparation of ALA Cyclopropyl Acetic Acid Fibrate: JIVA0029: Formula (II)

To a stirred solution of cyclopropyl acetic acid (3.06 g, 30.5 mmol) in anhydrous tetrahydrofuran (100 mL) cooled at −78° C., was added 2.0M LDA in THF (32.0 mL, 64.0 mmol). After addition, the reaction mixture was allowed to equilibrate to RT (30 mins) and then heated at 50° C. for one h to complete formation of the dianion. The mixture was cooled again to −78° C. and ALA bromide (10.0 g, 30.5 mmol) [as made in Example 1, Part 2] was added dropwise. The reaction mixture was stirred at RT overnight and then at 50° C. for four days. The reaction mixture was cooled to RT and then poured into ice-cold 1N hydrochloric acid (300 mL), extracted with methyl t-butyl ether (2×300 mL). The combined organic extracts were washed with brine (300 mL), dried over anhydrous sodium sulfate, and concentrated under reduced pressure, followed by purification through a silica gel flash chromatography eluting with heptane/ethyl acetate (from 50:1 to 10:1) to give the desired acid JIVA0029 (2.86 g pure, 3.31 g less pure, 61% total yield) as a light yellow oil, and further characterized by:

| Analysis: | |
|---|---|
| Appearance: | light yellow oil |
| Chemical Formula: | $C_{23}H_{38}O_2$ |
| Molecular Weight: | 346.29 |
| Chromatographic purity (HPLC): | 98.7% (rt = 9.525 min, isocratic MeOH, Synergi Max-RP, 5 μ 4.6 × 150 mm, 1.0 mL/min, 5 μL injection, 40° C., UV detection, 210 nm) |
| HRMS (ESI): | Calculated for $C_{23}H_{39}O_2$ (M + H)$^+$ 347.2945, found 347.2946. |
| $^1$H NMR (300 MHz, CDCl$_3$/TMS): | δ 11.50 (s, br, 1 H), 5.36 (m, 6 H), 2.81 (t, 4 H, J = 5.7 Hz), 2.05 (m, 4 H), 1.65 (m, 4 H), 1.28 (m, 12 H), 0.97 (t, 3 H, J =7.5 Hz), 0.55 (m, 2 H), 0.31 (m, 1 H), 0.17 (m, 1 H). |

Example 6: 2-Methyl-eicosa-11,14,17-trienoic acid (methyl-ALA-fibrate, JIVA 0037); Formula (I)

To a solution of propionic acid (226 mg, 3.05 mmol) in anhydrous THF (20 mL) at −20° C. was added dropwise, LDA (2M, 4.58 mL, 9.15 mmol). The mixture was warmed to 50° C. and stirred for 3 h. The solution was cooled again to −20° C. and a solution of ALA bromide [as made in Example 1, Part 3] (0.05 g, 1.53 mmol) in anhydrous THF (5 mL) was added dropwise. The reaction mixture was warmed to RT and stirred for 2 h, then 50° C. for 1 h. The reaction mixture was cooled in an ice bath and acidified with hydrochloric acid (1N, 30 mL). The product was extracted with ethyl acetate (3×30 mL). The combined ethyl acetate extracts were washed with water (30 mL) and brine (30 mL). The ethyl acetate solution was dried over sodium sulfate, filtered and concentrated.

The above reaction was repeated three times on the same scale. The crude product was purified twice by flash column chromatography on silica gel (60 g), eluting with 1-20% ethyl acetate/heptanes. The experiments generated 2-methyl-eicosa-11,14,17-trienoic acid (methyl-ALA-fibrate, JIVA 0037 as a colorless oil (0.80 g, 53% yield), and further characterized by:

| Analysis: | |
|---|---|
| Appearance: | colorless oil |
| Chemical Formula: | $C_{21}H_{36}O_2$ |
| Molecular Weight: | 320.51 |
| Chromatographic purity (HPLC): | 95.7% (rt = 9.621 min, 80-100% MeOH/H2O + 0.1% TFA) over 10 min., hold 10 min., Synergi Max-RP, 5 μ, 4.6 × 150 mm, 1.0 mL/min, 5 μL injection, 40° C., UV detection, 210 nm) |
| HRMS (ESI): | Calculated for C21H35O2 (M−H)⁻: 319.2643, found 319.2629. |
| ¹H NMR (300 MHz, CD₃OD/TMS): | δ 5.37 (m, 6 H), 2.81 (m, 4 H), 2.45 (m, 1H), 2.15-2.00 (m, 4 H), 1.67 (m, 1H), 1.40-1.25 (m, 10H), 1.17 (d, 3H, J = 8.7), 0.97(t, 3 H, J = 7.5 Hz). |
| ¹³C NMR (300 MHz, CD₃OD/TMS): | δ 183.4, 132.2, 130.6, 129.5, 127.9, 127.3, 39.6, 33.7, 29.8, 29.7, 29.6, 29.5, 27.5, 27.4, 25.8, 25.7, 20.8, 17.1, 14.5. |

Example 7: Preparation of 2-Isobutyl-eicosa-11,14,17-trienoic Acid Ethyl Ester; Formula (I); of the Structure Ethyl 4-methyl valerate (1.20 g, 8.3 mmol) was added to LDA (M, 9.0 mL, 9.0 mmol) in dry THF (20 mL) at −78° C. under an argon atmosphere. After 50 mins ALA iodide (2.0 g, 5.34 mmol) [as made in Example 1, Part 3] in HMPA (5 ML) was added dropwise. The reaction mixture was stirred for 4 hours at −78° C. and then was quenched with saturated ammonium chloride solution (20 mL), and the cooling bath was removed. Once the reaction reached RT, the product was extracted with diethyl ether (2×25 mL). The combined ether extracts, were washed with water. Toluene (20 mL) was added and the solution was dried over sodium sulfate, filtered, and concentrated. The remaining oil (2.8 g) was purified by column chromatography on silica gel (75 g), eluting with 100% heptane followed by 1% ethyl acetate in heptane. The experiment generated 2-isobutyl-eicosa-11,14, 17-trienoic acid ethyl ester 12 (1.4 g, 70% yield) as a colorless oil.

¹H NMR (300 MHz, CDCl₃/TMS): δ 5.36 (m, 6H), 4.10 (q, 2H, J=6.9 Hz), 2.79 (m, 4H), 2.38 (m, 1H), 2.10-1.98 (m, 4H), 1.1.53 (m, 1H), 1.40-1.25 (m, 10H), 1.00-0.82 (m, 12H).

Example 8: Preparation of 2-Isobutyl-eicosa-1,14,17-trienoic acid methylvalerate-ALA-fibrate; JIVA 0038; Formula (I) of the Formula 2-Isobutyl-eicosa-11,14,17-trienoic acid ethyl ester (1.4 g, 3.58 mmol) [as made in Example 5] was dissolved in THF (10 mL), ethanol (10 mL), and water containing sodium hydroxide (1.2 g, 32 mmol), and stirred under argon at RT for 48 h. To the reaction was added 10% aqueous hydrochloric acid solution and the reaction mixture was extracted with ethyl acetate (25 mL). The aqueous fraction was extracted a second time with ethyl acetate (25 mL). The combined ethyl acetate extracts were dried over sodium sulfate filtered and concentrated. The residual oil was filtered through silica gel (25 g) eluting with 5% ethyl acetate in heptane. The product 2-isobutyl-eicosa-11,14,17-trienoic acid methylvalerate-ALA-fibrate JIVA0038 (0.80 g, 62% yield) was obtained as a colorless oil, and further characterized by:

| Analysis: | |
|---|---|
| Appearance: | colorless oil |
| Chemical Formula: | $C_{24}H_{42}O_2$ |
| Molecular Weight: | 362.59 |
| Chromatographic purity (HPLC): | 99.5% (rt = 12.55 min, 80-100% MeOH/H2O + 0.1% TFA) over 10 min., hold 10 min., Synergi Max-RP, 5 μ, 4.6 × 250 mm, 1.0 mL/min, 5 μL injection, 40° C., UV detection, 210 nm) |
| HRMS (ESI): | Calculated for $C_{24}H_{41}O_2$ (M−H)⁻: 361.3112, found 361.3104. |
| ¹H NMR (300 MHz, CD₃OD/TMS): | δ 5.38 (m, 6 H), 2.80 (m, 4 H), 2.42 (m, 1H), 2.12-2.01 (m,4H), 1.65-1.54 (m, 3H), 1.30-1.20 (m, 10H), 0.97 (t, 3 H, J = 7.5 Hz) 0.90 (m, 6H). |
| ¹³C NMR (300 MHz, CD₃OD/TMS): | δ 182.9, 132.2, 130.6, 128.5, 127.9, 127.4, 43.7, 41.7, 32.9, 29.9, 29.8, 29.7, 29.6, 29.5, 27.6, 27.5, 26.4, 25.8, 25,7, 23.2, 22.6, 22.4, 20.8, 14.5. |

Detailed In Vitro Biology:

The following are procedures used for screening gamma-secretase modulating activity of Jiva compounds in cell cultures.

Protocol for Growing SHSY-5 Cells:

Fresh human neuroblastoma cells SHSY-5 were purchased from ATCC in the fall of 2105. All SHSY-5 cells were propagated and grown in p75 flasks, following the supplier's instructions. Briefly, SH-SY5Y cells were grown to confluence in Dulbecco's Modified Eagles Medium (DMEM) supplemented with 2 mM L-glutamine, 1× non-essential amino acids, and 0.22 micrometers filtered 10% heat inactivated fetal bovine serum (FBS) in a 5% $CO_2$ humidified incubator at 37° C. Cultures were split twice a week and cells were seeded at $2.5 \times 10^4$ cells/cm². The cells were detached from the bottles after two phosphate buffer washes that were followed by 5 min treatment with 0.25% trypsine solution.

Protocol for Preparation of Jiva Compounds and the Initial Screening:

Jiva compounds were dissolved under sterile conditions in different volumes of molecular biology grade dimethylsulfoxide (DMSO) so that the final concentration was 200 mM, with the goal to screen in a concentration range from 50 to 1000 μM. Thus, between 1 μL to 20 L of DMSO solution of each Jiva compound was added to 4 mL of sterile cell media with FBS adjusted to 1%. The cells were incubated with different compounds for 18 h (i.e. overnight). Following the incubation cells were tested for viability and morphology. The first viability criteria was attachment to the surface, the second viability criteria was resistance to trypan blue uptake. Only viable cells were harvested for ELISA screening.

Protocol for Cell Lysis

Confluent cells were scraped from p25 cell-culture bottles and collected in pellets by centrifugation for 5 mins at 1000 g. To measure intracellular amyloid β, the centrifugation helps in concentrating Aβ1-40 peptides for measurements. About 40 micro grams of cell can be recovered from 4 mL cell medium in p25 cell culture bottles. The cell pellets were re-suspended in RIPA buffer and incubated on ice for 30 min.

RIPA buffer means 150 mM sodium chloride; 1% NP-40; 0.5% sodium deoxycholate; 0.1% SDS; 50 mM Tris pH 8.0.

Following lysis, the cell debris was separated by centrifugation, 1 h at 40,000×g. The clear supernatant was collected for ELISA measurements that followed immediately after the centrifugation.

ELISA Protocol:

ELISA measurements used IBL ELISA kits for Aβ x-40 using manufacturer's protocol and supplied standards. Briefly, for each measurement 100 μL sample was prepared from 12.5 μL lysis buffer and 87.5 μL ASSAYBUF solutions in each well. ASSAYBUF solution were supplied in the kit, and used to incubate cell lysate with anti-amyloid antibody attached to the wells in ELISA plates. The plate covered with plate-lid was incubated with gentle shaking overnight at 4° C. Following the incubation lysis samples were washed with wash buffer that was supplied with the kit. Precisely, each well was filled with wash buffer for 15-30 seconds, and then drained with paper towels. The procedure was repeated 5 times.

In the next step 100 μL of enzyme conjugate solution was mixed with $2^{nd}$ antibody with conjugated HRP in each well and the test sample blank. The samples were incubated for 60 mins at 4° C. with gentle shaking covered with plate lid as recommended by the kit manufacturer. In the next step, the enzyme conjugate solution was washed 7 times in the same manner as earlier described.

In the last step, sample wells were incubated with HRP dye reagent 3, 3', 5, 5'-Tetramethylbenzidine (TMB). To each well was added 100 μL TMB solution that was supplied in the kit. Samples were incubated for 30 mins at RT in the dark, when the samples turned blue. TMB Stop Solution was added next, 100 μL, per well. Samples then turned yellow, and the sample optical density (OD) was measured at 450 nm against a reagent blank. The measurements were done within 30 mins after addition of TMB Stop Solution. The OD read outs were converted to pg/ml based on Aβ 1-40 standards that were supplied with the kits.

The following data were collected on the JIVA compounds indicated:

TABLE 1

| compound | incubated with drugs w cells microM | for analysis collected cells mg | average signal triplicates | stdev | sign-bkgr | signal nomalised to cells |
|---|---|---|---|---|---|---|
| JIVA 24 | 7.13 | 20 | 0.300 | 0.042 | 0.246 | 0.233 |
| JIVA 25 | 20 | 14 | 0.436 | 0.054 | 0.316 | 0.209 |
| JIVA 25 | 20 | 22 | 0:293 | 0.029 | 0.173 | 0.130 |
| JIVA 27 | 20 | 13 | 0.355 | 0.041 | 0.236 | 0.201 |
| JIVA 28 | 20 | 17 | 0.162 | 0.013 | 0.042 | 0.034 |
| JIVA 29 | 20 | 25 | 0.141 | 0.014 | 0.021 | 0.026 |
| SEMAGACESTAT | 2 | 31 | 0.12 | 0.009 | 0 | 0.000 |
| NO DRUGS | 0 | 21 | 0.315 | 0.034 | 0.195 | 0.194 |
| BKGR SIGNAL | 0 | 0 | 0.12 | 0.01 | 0 | 0.030 |
| | | 21.125 average cell mass | | | | |

Figure 1:
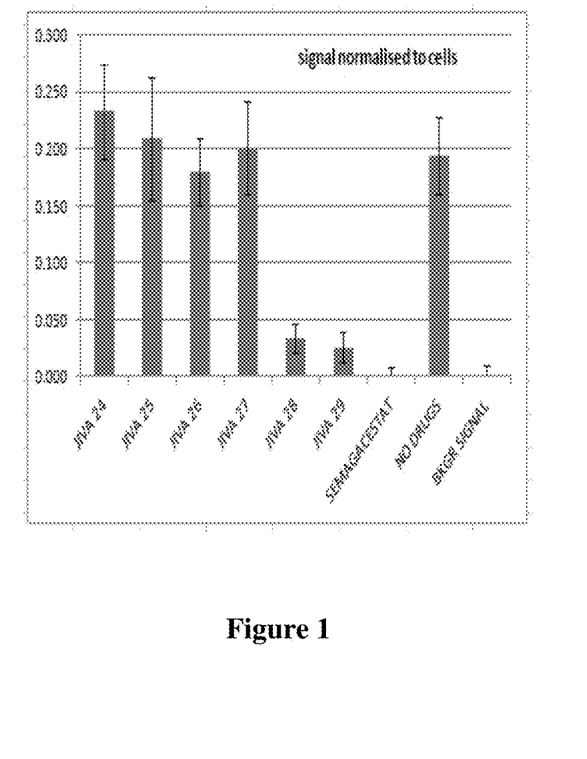
FIG. 1 graphically shows the data from 6 JIVA compounds and controls screened for gamma-secretase modulating activity in cell cultures of human neuroblastoma cells SHSY-5.

See FIG. 1 for a graph of this data.

Additional data on JIVA-0029 and JIVA-0028 are shown in the Tables below. These 2 compounds may be candidates for testing in the in vivo models of AD.

TABLE 2

| JIVA002B, | | first | | second | | third | |
|---|---|---|---|---|---|---|---|
| nM | LOG ([I], nM) | experiment 1 | bestfit1 | experiment 2 | bestfit2 | experiment 3 | bestfit3 |
| 0 | 0 | 102 | 100.0 | 104 | 100.0 | 99 | 100.0 |
| 21.4 | 1.3 | 101 | 100.0 | 103 | 100.0 | 104 | 100.0 |
| 74.1 | 1.9 | 98 | 99.8 | 102 | 99.9 | 108 | 99.9 |
| 100.0 | 2.0 | 102 | 99.8 | 99 | 99.9 | 97 | 99.9 |
| 213.8 | 2.3 | 101 | 99.5 | 95 | 99.7 | 100 | 99.7 |
| 741.3 | 2.9 | 97 | 98.5 | 100 | 99.1 | 94 | 99.0 |
| 1000.0 | 3.0 | 96 | 97.8 | 101 | 99.8 | 104 | 98.6 |

TABLE 2-continued

| JIVA002B, nM | LOG ([I], nM) | first | | second | | third | |
|---|---|---|---|---|---|---|---|
| | | experiment 1 | bestfit1 | experiment 2 | bestfit2 | experiment 3 | bestfit3 |
| 2138.0 | 3.3 | 90 | 95.4 | 98 | 97.5 | 90 | 97.1 |
| 7413.1 | 3.9 | 90 | 85.6 | 85 | 91.9 | 96 | 90.5 |
| 10000.0 | 4.0 | 88 | 81.5 | 85 | 89.4 | 85 | 87.7 |
| 21379.5 | 4.3 | 73 | 57.3 | 73 | 79.7 | 79 | 76.9 |
| 74131.0 | 4.9 | 28 | 37.2 | 46 | 53.1 | 57 | 48.9 |
| 100000.0 | 5.0 | 26 | 50.6 | 49 | 45.7 | 46 | 41.5 |
| 1000000.0 | 6.0 | 2 | 4.2 | 8 | 7.7 | 2 | 6.6 |
| calculated | IC50, microM | 44 | | 84 | | 71 | |

The numbers in red indicate concentration that showed decrease in cell viability

TABLE 3

| JIVA002B, nM | LOG ([I], nM) | first | | second | | third | |
|---|---|---|---|---|---|---|---|
| | | experiment 1 | bestfit1 | experiment 2 | bestfit2 | experiment 3 | bestfit3 |
| 0 | 0 | 102 | 100.0 | 104 | 100.0 | 99 | 100.0 |
| 21.4 | 1.3 | 101 | 99.9 | 103 | 100.0 | 104 | 100.0 |
| 74.1 | 1.9 | 98 | 99.7 | 102 | 99.9 | 108 | 99.8 |
| 100.0 | 2.0 | 102 | 99.6 | 99 | 99.6 | 97 | 99.5 |
| 213.8 | 2.3 | 101 | 99.1 | 95 | 99.6 | 100 | 99.5 |
| 741.3 | 2.9 | 97 | 97.0 | 100 | 98.6 | 94 | 98.3 |
| 1000.0 | 3.0 | 95 | 96.0 | 101 | 98.2 | 104 | 97.8 |
| 2138.0 | 3.3 | 90 | 91.8 | 98 | 96.2 | 90 | 95.4 |
| 7413.1 | 3.9 | 75 | 76.4 | 85 | 87.9 | 79 | 85.6 |
| 10000.0 | 4.0 | 71 | 70.6 | 85 | 84.4 | 72 | 81.5 |
| 21379.5 | 4.3 | 58 | 52.9 | 62 | 71.6 | 64 | 67.3 |
| 74131.0 | 4.9 | 18 | 14.5 | 46 | 42.1 | 33 | 37.2 |
| 100000.0 | 5.0 | 13 | 19.4 | 33 | 35.1 | 27 | 30.5 |
| 1000000.0 | 6.0 | 2 | 2.3 | 8 | 5.1 | 2 | 4.2 |
| calculated | IC50, microM | 24 | | 54 | | 44 | |

Figure 2:
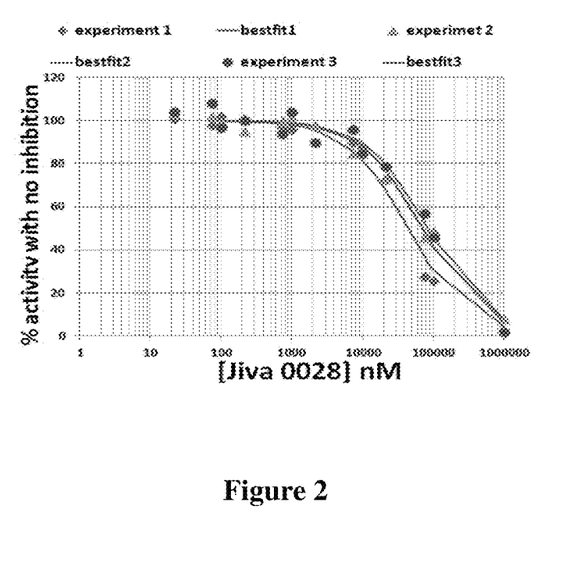
FIG. 2 graphically shows the data from JIVA 28 screened for gamma-secretase modulating activity in cell cultures of human neuroblastoma cells SHSY-5.
Figure 3:
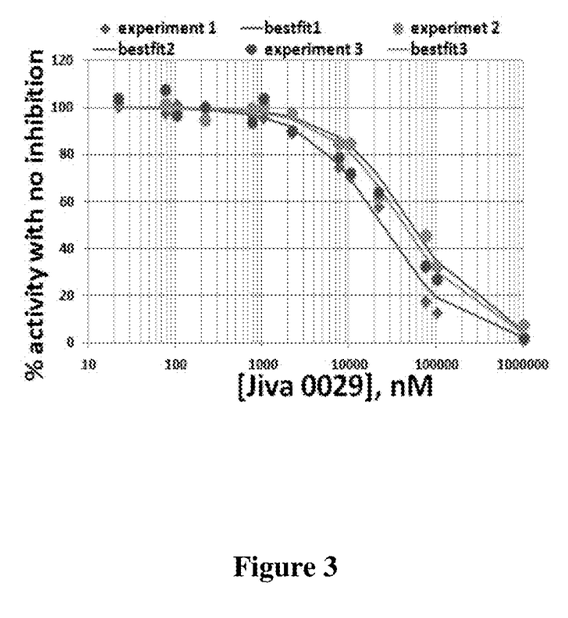
FIG. 3 graphically shows the data from JIVA 29 screened for gamma-secretase modulating activity in cell cultures of human neuroblastoma cells SHSY-5.

The numbers in red indicate concentration that showed decrease in cell viability See FIG. 2 for a graph of this data from Table 2; and FIG. 3 for a graph of this data from Table 3.

Compounds of Formula (I) and Formula (II) are preferably administered as a pharmaceutically-acceptable formulation having present pharmaceutically-acceptable adjuvants, binders, desiccants, diluents and excipients that are well known for such purpose. Such formulations are in the form of a solution for injection, ampoule, hard or soft gelatin capsule or tablet, or sustained release formulations. These formulations are used to treat persons for hypertriglyceridemia, cardiovascular disease, especially as gamma secretase modulators to treat mild cases of Alzheimer's disease, to treat hypertriglyceridemia, to treat cardiovascular disease by reducing triglycerides and for use as anti-inflammatory agents.

An effective amount of the active ingredient in the pharmaceutically-acceptable formulation is from about 0.05 to about 5 g/day, administered as 1-4 doses/day.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:

1. Compounds of Formula (I)

Formula (I)

wherein:

R is joined from the methylene moiety formed by reduction of the carboxylic acid of one of the following polyunsaturated fatty acids (PUFAs):

cis,cis,cis-7,10,13-hexadecatrienoic acid (HTA),
cis,cis,cis-9,12,15-octadecatrienoic acid (ALA),
cis,cis,cis,cis-6,9,12,15-octadecatetraenoic acid (SDA),
cis,cis,cis-11,14,17-eicosatrienoic acid (ETE),
cis,cis,cis,cis-8,11,14,17-eicosatetraenoic acid (ETA);
cis,cis,cis,cis,cis-5,8,11,14,17-eicosapentanenoic acid (EPA),
cis,cis,cis,cis,cis-6,9,12,15,18-heneicosapentaenoic acid (HPA), cis,cis,cis,cis,cis-7,10,13,16,19-docosapentaenoic acid (DPA),
cis,cis,cis,cis,cis-4,7,10,13,16,19-docosahexaenoic acid (DHA),
cis,cis,cis,cis-9,12,15,18,21-tetracosapentaeonic acid (TPA) or
cis,cis,cis,cis,cis-6,9,12,15,18,21-tetracosahexaeonic acid (THA); and $R_1$ is H;

$R_2$ is $C_1$-$C_6$ straight chain or branched alkyls; $C_3$-$C_6$ cycloalkyl; $C_3$-$C_6$ fluorocycloalkyl; $C_2$-$C_6$ alkenyl; $C_2$-$C_6$-alkynyl; $C_6$-$C_{10}$ aryl unsubstituted or substituted with $C_1$-$C_6$ straight chain or branched alkyls: $C_1$-$C_6$ alkoxyl; 1,3-dioxolanyl; cyano, halo, nitro, trihaloalkyl, acyl, or acylamino; alkylaryl unsubstituted or substituted with straight chain or branched alkyl; $C_1$-$C_6$ alkoxyl; 1,3-dioxolanyl; cyano, halo, trihaloalkyl, dialkylamino; or alkyldiaryls, or $R_1$ and $R_2$ are tethered together to form a 3- to 7-membered alicyclic ring, and the compound of Formula (I) can be a stereoisomer of either R or S configuration;

or its pharmaceutically-acceptable salts.

2. The compound of claim 1 of Formula (I), wherein the $R_1$ and $R_2$ moieties are tethered together, forming a compound of Formula (II)

Formula (II)

wherein: n=1-4; and R is as defined in claim 1.

3. The compound of claim 1 which is 2-cyclopropyl-cis,cis,cis,cis,cis-7,10,13,16,19-docosapentaenoic acid; JIVA-0028; EPA cyclopropyl acetic acid-fibrate, having the structure 4. The compound of claim 1 which is 2-cyclopropyl-eicosa-11,14,17-trienoic acid (JIVA 0029), having the structure 5. The compounds of claim 1 wherein the compound has a chemical purity of ≥90% by weight.

6. A pharmaceutical formulation having as its active ingredient one or more compounds of Formula (I) as defined in claim 1 and pharmaceutically-acceptable salts, with one or more adjuvants, binders, desiccants, diluents and excipients.

7. The pharmaceutical formulation of claim 6 as a solution for injection, ampoule, hard or soft gelatin capsule or tablet, or as a sustained release formulation.

8. The pharmaceutical formulation of claim 6 for the treatment of Alzheimer's disease in a person needing such treatment by administering to such person an effective amount of the formulation.

9. The pharmaceutical formulation of claim 6 to treat hypertriglyceridemia, or cardiovascular disease in persons needing such treatment by administering to such persons an effective amount of the formulation.

10. The pharmaceutical formulation of claim 9, wherein the triglycerides levels in such persons needing treatment are in a range of from >100 mg/dl, to >500 mg/dl.

11. The pharmaceutical formulation of claim 9, wherein the effective amount is from about 0.05 to about 5 g/day, administered as 1-4 doses/day.

12. Compounds of Formula (II)

Formula (II)

wherein: n=1-4; and

R is joined from the methylene moiety formed by reduction of the carboxylic acid of one of the following polyunsaturated fatty acids (PUFAs):
cis,cis,cis-7,10,13-hexadecatrienoic acid (HTA),
cis,cis,cis-9,12,15-octadecatrienoic acid (ALA),
cis,cis,cis,cis-6,9,12,15-octadecatetraenoic acid (SDA),
cis,cis,cis-11,14,17-eicosatrienoic acid (ETE),
cis,cis,cis,cis-8,11,14,17-eicosatetraenoic acid (ETA);
cis,cis,cis,cis,cis-5,8,11,14,17-eicosapentanenoic acid (EPA),
cis,cis,cis,cis,cis-6,9,12,15,18-heneicosapentaenoic acid (HPA),
cis,cis,cis,cis,cis-7,10,13,16,19-docosapentaenoic acid (DPA),
cis,cis,cis,cis,cis-4,7,10,13,16,19-docosahexaenoic acid (DHA),
cis,cis,cis,cis-9,12,15,18,21-tetracosapentaeonic acid (TPA) or
cis,cis,cis,cis,cis-6,9,12,15,18,21-tetracosahexaeonic acid (THA); and the compound of Formula (I) can be a stereoisomer of either R or S configuration, or its pharmaceutically-acceptable salts.

13. The compound of claim 12 which is 2-cyclopropyl-cis,cis,cis,cis,cis-7,10,13,16,19-docosapentaenoic acid; JIVA-0028; EPA cyclopropyl acetic acid-fibrate, having the structure

14. The compound of claim 12 which is 2-cyclopropyl-eicosa-11,14,17-trienoic acid (JIVA 0029), having the structure

* * * * *